United States Patent
Lunn et al.

[19]

[11] Patent Number: 6,106,510
[45] Date of Patent: Aug. 22, 2000

[54] EXTRUDED GUIDE CATHETER SHAFT WITH BUMP EXTRUSION SOFT DISTAL SEGMENT

[75] Inventors: Peter A. Lunn, Beverly; Nasser Rafiee, Andover, both of Mass.; David J. Lentz, LaJolla, Calif.; Peter G. Strickler, Beverly, Mass.

[73] Assignee: Medtronic, Inc., Minneapolis, Minn.

[21] Appl. No.: 09/086,074

[22] Filed: May 28, 1998

[51] Int. Cl.[7] .............................. A61M 25/00; A61B 6/00
[52] U.S. Cl. .................... 604/525; 604/523; 604/524; 604/526; 604/264; 604/532; 600/433
[58] Field of Search ............... 604/264, 523–28, 604/532; 600/433, 435

[56] References Cited

U.S. PATENT DOCUMENTS

| | | | |
|---|---|---|---|
| 4,596,563 | 6/1986 | Pande | 604/264 |
| 4,904,431 | 2/1990 | O'Maleki | 264/103 |
| 4,925,710 | 5/1990 | Buck et al. | 428/34.5 |
| 4,963,306 | 10/1990 | Weldon | 264/101 |
| 5,125,913 | 6/1992 | Quackenbush | 604/264 |
| 5,316,706 | 5/1994 | Muni et al. | 264/25 |
| 5,318,032 | 6/1994 | Lonsbury et al. | 128/658 |
| 5,533,985 | 7/1996 | Wang | 604/264 |
| 5,542,937 | 8/1996 | Chee et al. | 604/264 |
| 5,676,659 | 10/1997 | McGurk | 604/525 |
| 5,702,373 | 12/1997 | Samson | 604/525 |
| 5,730,733 | 3/1998 | Mortier et al. | 604/527 |
| 5,755,704 | 5/1998 | Lunn | 604/526 |
| 5,851,203 | 12/1998 | Van Muiden | 604/525 |
| 5,876,385 | 3/1999 | Ikari et al. | 604/523 |
| 5,891,110 | 4/1999 | Larson et al. | 604/523 |
| 5,902,284 | 5/1999 | Suzuki et al. | 604/265 |

FOREIGN PATENT DOCUMENTS

| | | | |
|---|---|---|---|
| WO 96/20750 | 7/1996 | European Pat. Off. | A61M 25/00 |
| WO 97/14466 | 4/1997 | European Pat. Off. | A61M 25/00 |

*Primary Examiner*—Glenn K. Dawson
*Assistant Examiner*—Patricia Bianco

[57] ABSTRACT

A medical catheter including a continuous liner defining a guidewire lumen. The liner has a constant inner diameter and a constant outer diameter. A continuous layer is braided over the liner and encapsulated between the liner and a bump layer. The bump layer has a proximal segment, and a bump section. The bump section has a transition zone at the proximal end of the bump section. The proximal segment has a distal end affixed to the proximal end of the bump section. The proximal segment of the bump layer has an outer diameter which is less than the outer diameter of the bump section of the bump layer. The transition zone has an outer diameter which smoothly transitions from the outer diameter of the distal end of the proximal segment of the bump layer to the larger outer diameter at the distal end of the transition zone. The bump layer is encapsulated between the outer jacket layer and the braided layer. The outer jacket layer has a constant outer diameter and an inner diameter conforming to the variable outer diameter of the bump layer. The bump layer is made of a material with a greater flexural modulus than that of the outer jacket layer, such that the flexibility of the catheter is greater at the distal end of the catheter than at the proximal end of the catheter.

12 Claims, 2 Drawing Sheets

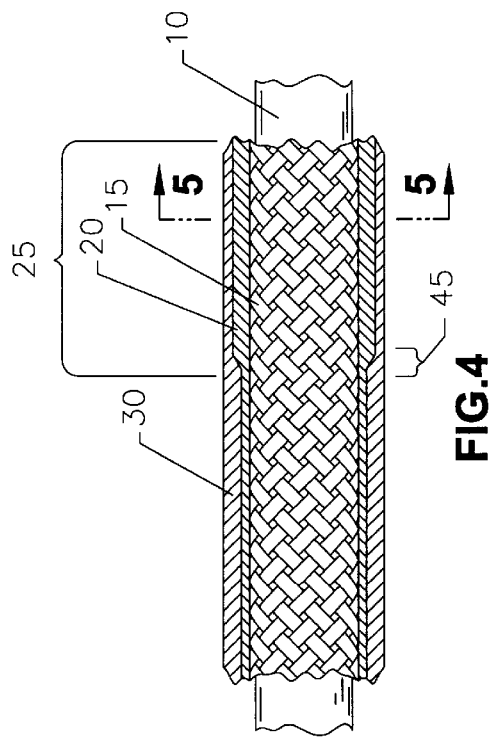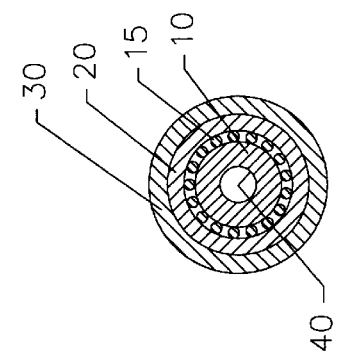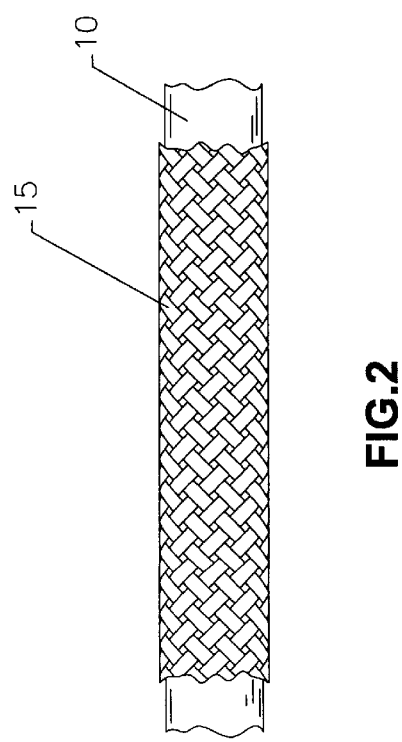

6,106,510

EXTRUDED GUIDE CATHETER SHAFT WITH BUMP EXTRUSION SOFT DISTAL SEGMENT

FIELD OF THE INVENTION

The present invention relates to guiding catheters and more particularly to the use of bump extrusion in altering the flexural modulus of a catheter shaft.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall.

Although the dimensions in the above example are suited to the coronary arteries, any body lumen can be treated by percutaneous transluminal angioplasty (PTA), including the vas deferens, ducts of the gallbladder, prostate gland, trachea, bronchus and liver. The body lumens range in diameter from small coronary vessels of 3 mm or less to 28 mm in the aortic vessel. The invention applies to acute and chronic closure or reclosure of body lumens.

Soft distal segments are advantageous in guiding catheters for navigating tortuous paths in the vascular system. This has been achieved in the prior art by attaching discrete softer segments with varying durometer material to the distal end of a guiding catheter. As for example, commonly owned copending patent application for an Improved Method of Soft Tip Forming, U.S. Ser. No. 08/368/186 to Riopel and Horrigan as well as commonly owned copending patent application for a Guide Catheter with Soft Distal Segment, U.S. Ser. No. 08/543,992 to Brin et al. Discrete segments have the disadvantage of the possibility of joint separation. Joining multiple pieces requires more manufacturing time then would an extrusion. Buckling and kinking can also occur at joints where there is an abrupt transition in stiffness.

U.S. Pat. No. 4,904,431 to O'Maleki for "Process for Manufacturing Catheters" discloses a continuous extrusion of a first rigid polymer to form a cylindrical body which will define the inner rigid sheath of the catheter. A second soft, pliable polymer is then extruded over this cylindrical body to form an outer cylindrical layer, which will define the outer soft, pliable sheath of the catheter. Another embodiment involves reinforcing the cylindrical bodies with a stiffening material, typically a wire cord wrapped around the inner layer and embedded between the inner and outer sheaths of the catheter. The rigid polymer is extruded at a variable rate which is altered at prescribed locations to first successively diminish the thickness of the forming layer, and then successively increase the thickness, thus forming a depression. This location will form the tip region of two catheters. The overlaying of this location, during the second extrusion step, with the soft polymeric material will define the soft catheter tip. The final catheters are formed by cutting the resulting structure at the junction of where the thickness of the first forming layer begins to increase in thickness.

U.S. Pat. No. 5,533,985 to Wang for "Tubing" discloses in FIG. 10 "bump" tubing in which the insert end is of stiffer material and the bell end is of soft material.

What is needed is a means of attaching separate segments of catheter shaft to provide a soft distal segment on a high volume, low cost basis. It is an object of the invention to provide a continuous outer jacket, a continuous braided layer and a continuous liner throughout the length of the product resulting in greater safety while having a distal segment with a lower flexural modulus than the proximal segment. It is another object of the invention to improve kink resistance in the distal segment.

SUMMARY OF THE INVENTION

The present invention is accomplished by providing a method and apparatus for a medical catheter comprising a continuous liner defining a guidewire lumen. The liner has a constant inner diameter and a constant outer diameter. A continuous layer is braided over the liner and encapsulated between the liner and a bump layer. The bump layer has a proximal segment, and a bump section. The bump section has a transition zone at the proximal end of the bump section. The proximal segment has a distal end affixed to the proximal end of the bump section. The proximal segment of the bump layer has an outer diameter which is less than the outer diameter of the bump section of the bump layer. The transition zone has an outer diameter which smoothly transitions from the outer diameter of the distal end of the proximal segment of the bump layer to the larger outer diameter at the distal end of the transition zone. The bump layer is encapsulated between the outer jacket layer and the braided layer. The outer jacket layer has a constant outer diameter and an inner diameter conforming to the variable outer diameter of the bump layer. The bump layer is made of a material with a lower flexural modulus than that of the outer jacket layer, such that the flexibility of the catheter is greater at the distal end of the catheter than at the proximal end of the catheter.

BRIEF DESCRIPTION OF THE DRAWINGS

FIG. 2 is a view of the liner and braided layer of a guiding catheter;

FIG. 3 is a longitudinal cross-section view of the liner, braided layer and bump extrusion layer;

FIG. 4 is a longitudinal cross-section view of the liner, braided layer, bump extrusion layer and outer jacket of the preferred embodiment;

FIG. 5 is a cross-section of FIG. 4 along the lines 5—5 of the preferred embodiment;

DETAILED DESCRIPTION OF THE PREFERRED EMBODIMENTS

Figure 1:
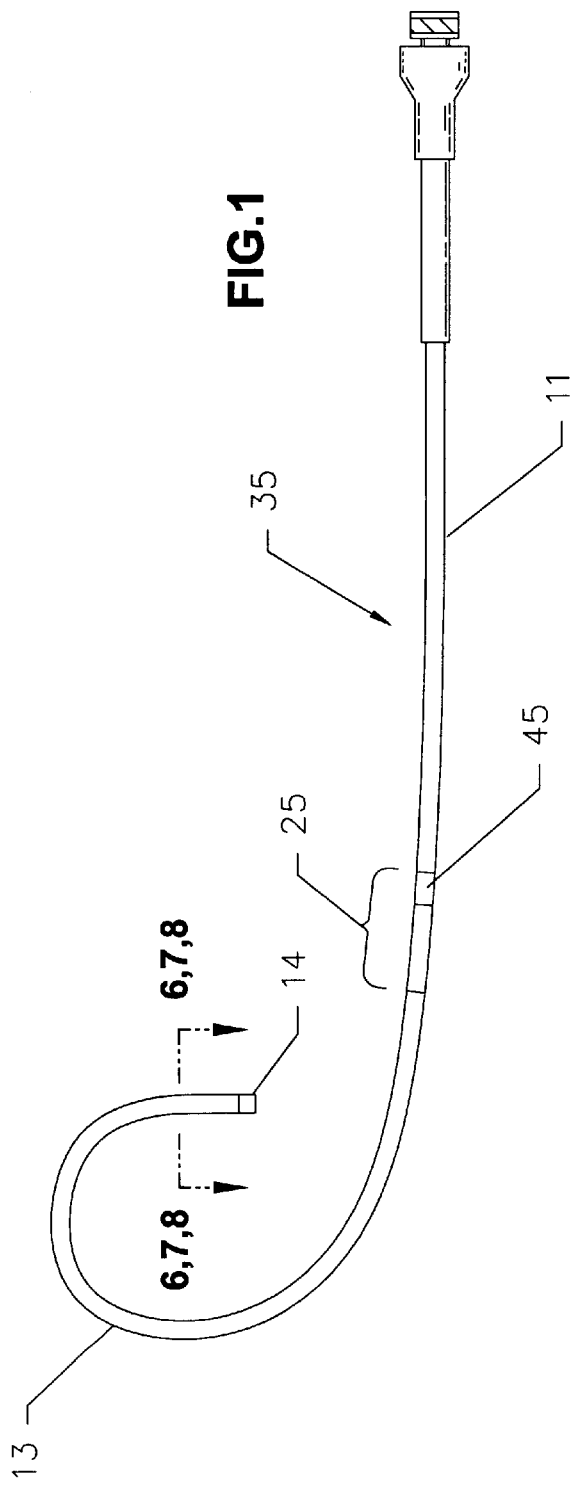
FIG. 1 is an overall view of a guiding catheter.

It is advantageous for guiding catheters 35 to have a stiff proximal segment 11 for pushability and torqueability while having a softer, more flexible distal segment 13 for navigating tortuous vessels and resulting in less trauma to the vessel walls. Applicant's invention provides a means of creating a stiff proximal segment 11 with a soft distal segment 13 in a guide catheter 35 using continuous extrusion and braiding technologies.

Applicant's "bump" extrusion technology alters the flexural modulus of the distal segment 13 of the guiding catheter 35. The preferred embodiment seen in FIG. 4 provides a continuous outer jacket 30 over the continuous bump extrusion layer 20, overlaying a continuous braided layer 15 with a continuous liner 10 within which defines a guidewire lumen 40. The continuous layers throughout the length of the guiding catheter 35 result in greater safety as there are no junctures were adjoined tubing pieces can break. The joining of two plastic tubes with tubes of a different stiffness by secondary operations such as melt bonding, molding or radio frequency bonding as in the prior art is avoided, thereby avoiding kinking at the juncture. Kink resistance is improved in the distal segment 13 because the layers are continuously extruded. This eliminates discrete, separately joined segments, which results in less manufacturing cost, reduced manufacturing time and greater safety.

Applicant's guiding catheter is designed as follows. The innermost layer is an optional liner 10 which defines the guidewire lumen 40. The liner 10 is formed by extruding a rigid thermoplastic elastomer polymer such as PEBAX® (available from the Elf Atochem Corporation, Philadelphia, Pa.), or Vestamid® which is a Polyamid 12 (available from Huls America Inc., Turner Place, Piscataway, N.J. 08855-0365), over an optional substrate material such as polyacetal. The liner 10 could also be formed of a Polyamid such as Vestamid®, Nylon 12, or Nylon 6. Thermoplastic urethanes such as Tecoflex® available from Thermedics, Inc., Woburn Mass. 01188-1799 or Tecothane® available from Thermedics, Inc., Woburn Mass. 01188-1799?), etc. could also be used as the liner 10. In addition, ECTFE (Ethelene ChloroTriFluoro Ethylene, a melt processable fluoropolymer available from Ausimont USA) material such as Halar® could be used and optionally extruded over a substrate such as polyacetal to form the liner 10.

The advantage of the ECTFE material is that it exhibits melt processibility unlike other fluoropolymers such as PTFE (polytetrafluoroethylene) Teflon, a registered trademark of the E. I. Du Pont de Nemours & Company, Wilmington, Del. This melt processibility permits the overextrusion and bonding of the fluoropolymer with thermoplastic outer jacket materials such as PEBAX® to produce a laminated catheter assembly. The ECTFE material also exhibits a coefficient of friction, which is substantially lower than material such as PEBAX® which is beneficial for the passage of interventional therapeutic devices through the lumen of the liner. A fluoropolymer such as FEP (fluorinated ethylene propylene copolymer) available from Daikin America, Inc., 20 Olympic Drive, Orangeberg, N.Y. 10962, exhibits melt processibility but is not well suited for wall thicknesses of 0.001 inches or less because of its relatively low melt strength and high melt viscosity, compared to a material such as PEBAX®, which results in melt fracture at these wall thicknesses. Additionally the low melt strength and high melt viscosity of FEP causes stress cracking which makes FEP undesirable for thin wall catheter applications. In contrast, ECTFE exhibits melt strength and viscosity which is sufficient to permit extruded all thicknesses of 0.001 inches or less.

Additional fluoropolymer groups which exhibit melt processibility, applicability for wall thicknesses less than 0.001 inches, and low frictional coefficients are the copolymers MFA and PFA which are marketed under the tradename HYFLON® and are obtainable from Ausimont USA. MFA and PFA exhibit frictional coefficients which are approximately equivalent to PTFE and are lower than ECTFE. Thus, a material such as HYFLON® is preferred for its melt processibility, thin wall capability, and coefficient of friction.

Heretofore a catheter utilizing a PTFE or FEP fluoropolymer liner required a chemical etchant to permit bonding of the jacket to the liner and the PTFE liner. This chemical etchant is generally costly and has adverse environmental impact. Using a material such as ECTFE, MFA, or PFA permits a technique known as plasma etching to accomplish bonding with a catheter jacket. The plasma etching utilizes a corona discharge method of displacing fluorine atoms from the surface of the fluoropolymer which lowers the surface energy of the fluoropolymer and permits greater wetting and consequently bonding of the catheter jacket to the liner. The corona discharge method enjoys both a cost and an environmental advantage over chemical etching techniques.

For braided catheters, polyacetal must be used to keep the liner 10 from collapsing. In general, the substrate is used for tolerance improvement and reducing wall thickness in tube extrusion if required and is necessary during braiding to prevent the lumen from collapsing. The disadvantages of a substrate are those of the addition of the secondary operation of removing the Polyacetal beading/core after extrusion as well as the additional costs. The core is removed after the liner 10, braiding 15 and outer jacket 30 has been extruded. The preferred materials for use in the liner 10 are those which exhibit lubricious qualities thereby facilitating the passage of devices. The liner 10 will have a constant inner diameter and a constant outer diameter. The liner is optional and is depicted in FIGS. 2–6. A guiding catheter could also be designed without a liner 10 as seen in the FIGS. 7 and 8 cross-sections.

Figure 8:
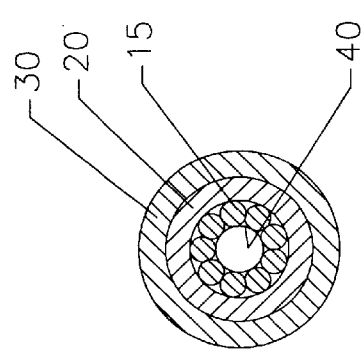
FIG. 8 is a cross-section of FIG. 1 along the lines 8—8 of an alternative embodiment.
Figure 7:
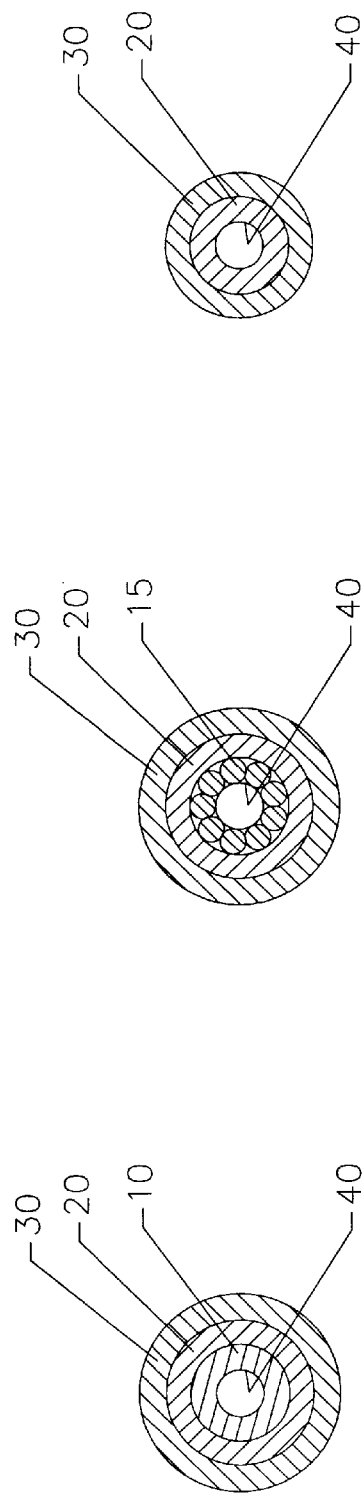
FIG. 7 is a cross-section of FIG. 1 along the lines 7—7 of an alternative embodiment.
Figure 6:
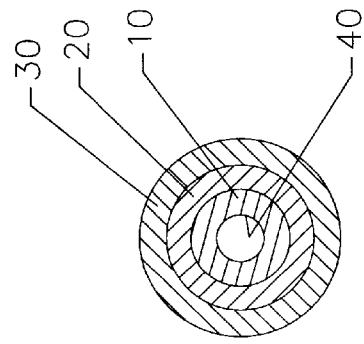
FIG. 6 is a cross-section of FIG. 1 along the lines 6—6 of an alternative embodiment.

Optional braided layer 15 is applied over the liner 10 as seen in FIGS. 2–5. It would be possible to have the braided layer 15 without a liner 10 as seen in FIG. 7 or no braided layer 15 at all as seen in FIGS. 6 and 8. The braiding may be formed of conventional material such as at least half hard stainless steel S.S. 304. The outer diameter of the braided layer 15 is approximately 0.085 inches thick. The advantage of braided layer 15 is that of improved torque, kink resistance and pushability.

The bump extrusion layer 20 is applied over the braided layer 15 as seen in FIGS. 3–5 and 7. If the braided layer 15 is encapsulated between the liner 10 and the bump extrusion layer 20 as seen in FIGS. 3–5, torque, kink resistance and pushability will be improved. Encapsulation occurs when the braided layer 15 is bonded between the braid picks to another layer. The pick count is the number of wire group intersections per inch. The pic count should be greater than about 25 to 30 to retain sufficient kink resistance and less than about 70–75 to retain sufficient torque transfer. A pic count of about 50 is preferred. The bump extrusion layer 20 may also be applied directly over the liner 10 as seen in FIG. 6. The bump extrusion layer 20 need not have any layer underneath it as seen in FIG. 8.

The first pass of the extruder lays the bump extrusion layer 20 which consists of a fine layer of soft material such as PEBAX® 63D, PEBAX® 55D, PEBAX® 40D, or a Vestamid® E-series such as E-40 or E-62 for the length of the proximal segment 11. Other material appropriate for the bump extrusion layer 20 include thermoplastic elastomer and thermoplastic urethanes, polyamids and PEBA (polyether block amide copolymer) materials that exhibit similar soft properties. A typical catheter is about 100 inches long with the length of the proximal segment 11 being about 44 inches. The soft distal segment 13 is the balance of the length, or 66 inches. The bump extrusion layer 20 may be formed of a plastic material having a lower flexural modulus than the outer jacket 30. A suitable range of material for the bump extrusion layer 20 for example, is a 35D Durometer to 55D Durometer material. The bump extrusion layer 20 in the proximal segment 11 can be approximately 0.001 inches to 0.0015 inches thick with an outer diameter of approximately 0.090 inches and a length of approximately 42 to 46 inches. The bump section 25 in the bump extrusion layer 20 can be approximately 0.004 inches to 0.005 inches thick with an outer diameter increasing to approximately 0.097 inches thick. The thickness of the bump section 25 can be tailored to the specific application. Guiding catheters with thinner walls would have a thinner bump section 25 then would angiography catheters, for example, with thicker walls. The length of the bump section 25 is approximately 4–7 inches long.

A transition zone 45 of preferably 0 inches to 1.5 inches in length, links the soft distal segment 13 and the proximal segment 11. The length of transition zone 45 depends on how fast the puller responds to speed change, on the distance between the puller, on the die landing and on the melt volume capacity of the melt pump which should be as low as possible. A low melt volume capacity is necessary in an optimized process which requires minimum melt in order to make the transition from bump 25 to transition zone 45 significantly easier. Otherwise, the excess melt will create die swell during puller speed change and it will result in a non-uniform diameter. The purpose of the transition zone 45 is to minimize catheter kink, especially if the catheter shaft 11 stiffness is significantly higher (e.g., PEBAX® 72D, Vestamid® 75D) than the bump 25 area (e.g., PEBAX® 35D, Vestamid® 40D).

The second pass of the extruder lays the outer jacket layer 30 over the bump extrusion layer 20. The outer jacket 30 may be formed of a plastic material having a high flexural modulus than the bump extrusion layer 20. A suitable range, for example, is a 70 Durometer to 85 Durometer material such as PEBAX® 70D or Vestamid® L-series. Most thermostatic elastomers, thermostatic urethane, PEBA and polyamids with a flexural modulus from 110,000 psi to 210,000 psi would be suitable. The outer jacket layer 30 will have a constant outer diameter.

Bump extrusion can be accomplished by using either two separate extrusion passes (one for the bump extrusion layer 20 and another for the outer jacket layer 30) or by using co-extrusion technology to simultaneously extrude both layers. In either case the thermoplastic material must be melt compatible and process compatible. Co-extrusion is preferable to multiple extrusion passes because of its lower cost as well as shorter run and processing time; the end product is the same.

To co-extrude, use a co-extrusion crosshead die (including an extruder screw, breaker plate and screen pack) with one, one inch extruder. For bump extrusion, only one extruder and one puller are required at any given time. The system also includes a very low volume Servo melt pump with a pressure feed back loop available from Killion Extruders, Inc., Davis-Standard Corp., 200 Commerce Road, Cedar Grove, N.J. The system also requires a Servo driven bump tube puller with a control package such as Allen Brady's Program Logic Controller (PLC) and an on line laser mike. The extruders, the melt pumps, the laser mike and the puller are controlled through the PLC with a Bump/variable stiffness software program which controls variables such as the extruder speed, the melt pump and the programmable puller. The PLC can be programmed according to the application's needs.

The first one inch extruder is held at a constant speed producing the outer jacket 30. The speed of the servo melt pump is varied by the controller as the servo bump tube puller speed varies to alternate the ratio of the outer jacket layer 30 and the bump extrusion layer 20 while holding a constant outer diameter for the jacket layer 30. The puller has a variable speed which draws the polymer out of the extruder. The thickness of the polymer being extruded is manipulated by varying the speed at which the polymer is being drawn by the puller. The puller is programmed to gradually increase or decrease the speed of the drawing rate of the polymer through the die of the extruder. This co-extruded layer can be laid over the optional braided layer 15.

A soft tip 14 could be affixed to the distal end of the catheter 35 by a variety of prior art means known to those skilled in the art.

FIRST EXAMPLE

Bump Extrusion Layer 20 Material—Unfilled 40D PEBAX®

Puller Speed—25/6ft./min.

Die 1 and 2—425 degrees

Clamp Ring—425 degrees

Extruder Zone 1—224 degrees

Extruder Zone 2—295 degrees

Extruder Zone 3—425 degrees

Result—Acceptable

SECOND EXAMPLE

Bump Extrusion Layer 20 Material—40D PEBAX® filled with 40% barium sulfate

Puller Speed—25/6ft./min.

Die 1 and 2—425 degrees

Clamp Ring—425 degrees

Extruder Zone 1—224 degrees

Extruder Zone 2—295 degrees

Extruder Zone 3—425 degrees

Result—Acceptable, the transition zone 45 to bump section 25 is smooth but at the end of the bump section 25 the transition zone 45 was not as smooth.

THIRD EXAMPLE

Bump Extrusion Layer 20 Material—70D PEBAX® from the Elf Atochem Corp.,

Philadelphia, Pa.

Puller Speed—15ft./min.—No melt pump

Die 1 and 2—425 degrees

Clamp Ring—425 degrees

Extruder Zone 1—224 degrees

Extruder Zone 2—295 degrees

Extruder Zone 3—425 degrees

Result—Imperfections and thickness variation perhaps because there was no melt pump.

FOURTH EXAMPLE

Bump Extrusion Layer 20 Material—Polyacetal available from Dunn Industries, 123 Abby Road, Manchester, N.H. 03103
Melt Pump added
Die 1 and 2—425 degrees
Clamp Ring—425 degrees
Extruder Zone 1—224 degrees
Extruder Zone 2—295 degrees
Extruder Zone 3—425 degrees Result—Polyacetal beading material could not hold up to the temperature coming out of the die and the coating kept slipping.

Different puller speeds were used which result in different thicknesses depending on the material used.

First Run Puller Speed—48/12 ft./min
Second Run Puller Speed—60/25 ft./min
Third Run Puller Speed—10/50 ft./min.

The preceding specific embodiments are illustrative of the practice of the invention. It is to be understood, however, that other expedients known to those skilled in the art or disclosed herein, may be employed without departing from the scope of the appended claims.

| No. | Component |
|---|---|
| 10 | Liner |
| 11 | Proximal Segment |
| 13 | Soft Distal Segment |
| 14 | Soft Tip |
| 15 | Braided Layer |
| 20 | Bump Extrusion Layer Proximal Section |
| 25 | Bump Section |
| 30 | Outer Jacket |
| 35 | Guide Catheter |
| 40 | Guidewire Lumen |
| 45 | Transition Zone |

What is claimed is:

1. A medical catheter, comprising:
   a continuous liner defining a guidewire lumen, the liner having a constant inner diameter and a constant outer diameter;
   a continuous braided layer being braided over the continuous liner, the braided layer having a constant inner diameter and a constant outer diameter;
   a continuous bump layer, the braided layer being encapsulated between the liner and the bump layer;
   the bump layer having a proximal segment, and a bump section, the bump section having a transition zone at a proximal end of the bump section, the proximal segment having a distal end affixed to the proximal end of the bump section;
   the proximal segment of the bump layer having an outer diameter which is less than an outer diameter of the bump section of the bump layer, the transition zone having an outer diameter which smoothly transitions from the outer diameter of the distal end of the proximal segment of the bump layer to the larger outer diameter at a distal end of the transition zone; and
   a continuous outer jacket layer, the bump layer being encapsulated between the outer jacket layer and the braided layer, the outer jacket layer having a constant outer diameter, the outer jacket layer having an inner diameter conforming to the variable outer diameter of the bump layer, the bump layer being made of a material with a lower flexural modulus than that of the outer jacket layer, such that the flexibility of the catheter is greater in the bump section than in the proximal segment.

2. A medical catheter, comprising:
   a continuous liner defining a guidewire lumen, the liner having a constant inner diameter and a constant outer diameter;
   a continuous bump layer encapsulating the liner;
   the bump layer having a proximal segment, and a bump section, the bump section having a transition zone at a proximal end of the bump section, the proximal segment of the bump layer having a distal end affixed to the proximal end of the bump section;
   the proximal segment of the bump layer having an outer diameter which is less than an outer diameter of the bump section of the bump layer, the transition zone having an outer diameter which smoothly transitions from the outer diameter of the distal end of the proximal segment of the bump layer to the larger outer diameter at a distal end of the transition zone; and
   a continuous outer jacket layer, the bump layer being encapsulated between the outer jacket layer and the liner, the outer jacket layer having a constant outer diameter, the outer jacket layer having an inner diameter conforming to the variable outer diameter of the bump layer, the bump layer being made of a material with a lower flexural modulus than that of the outer jacket layer such that the flexibility of the catheter is greater in the bump section than in the proximal segment.

3. A medical catheter, comprising:
   a continuous liner defining a guidewire lumen, the liner having a constant inner diameter and a constant outer diameter;
   a continuous braided layer being braided over the continuous liner, the braided layer having a constant inner diameter and a constant outer diameter;
   a continuous bump layer;
   the bump layer having a proximal segment, and a bump section, the bump section having a transition zone at a proximal end of the bump section, the proximal segment having a distal end affixed to the proximal end of the bump section;
   the proximal segment of the bump layer having an outer diameter which is less than an outer diameter of the bump section of the bump layer, the transition zone having an outer diameter which smoothly transitions from the outer diameter of the distal end of the proximal segment of the bump layer to the larger outer diameter at a distal end of the transition zone; and
   a continuous outer jacket layer, the bump layer being encapsulated between the outer jacket layer and the braided layer, the outer jacket layer having a constant outer diameter, the outer jacket layer having an inner diameter conforming to the variable outer diameter of the bump layer, the bump layer being made of a material with a lower flexural modulus than that of the outer jacket layer such that the flexibility of the catheter is greater in the bump section than in the proximal segment.

4. A medical catheter comprising;
   a continuous bump layer;
   the bump layer having a proximal segment, and a bump section, the bump section having a transition zone at a proximal end of the bump section, the proximal segment having a distal end affixed to the proximal end of the bump section;

the proximal segment of the bump layer having an outer diameter which is less than an outer diameter of the bump section of the bump layer, the transition zone having an outer diameter which smoothly transitions from the outer diameter of the distal end of the proximal segment of the bump layer to the outer diameter at a distal end of the transition zone; and a continuous outer jacket layer encapsulating the bump layer, the outer jacket layer having a constant outer diameter, the outer jacket layer having an inner diameter conforming to the variable outer diameter of the bump layer, the bump layer being made of a material with a lower flexural modulus than that of the outer jacket layer such that the flexibility of the catheter is greater in the bump section than in the proximal segment.

5. A medical catheter according to any of claims 1–2 wherein the liner further comprises an extrusion of a rigid, thermoplastic, elastomer polymer over polyacetal.

6. A medical catheter according to any of claims 1–4 wherein the thickness of the proximal segment of the bump layer is approximately 0.001 to 0.0015 inches.

7. A medical catheter according to any of claims 1–4 wherein the thickness of the bump section of the bump layer ranges from between approximately 0.004 inches to approximately 0.005 inches.

8. A medical catheter according to any of claims 1–4 wherein the bump layer is made of a material with a durometer ranging from approximately 35D to 55D.

9. A medical catheter according to any of claims 1–4 wherein the bump section has a length from approximately 4 inches to approximately 7 inches.

10. A medical catheter according to any of claims 1–4 wherein the transition zone has a length of not greater than approximately 12 inches.

11. A medical catheter according to any of claims 1–4 wherein the outer jacket is formed of a material with a flexural modulus greater than that of the material of the bump layer.

12. A medical catheter according to any of claim 1 or 3 wherein the braided layer has a pic count of between approximately 25–75.

* * * * *